United States Patent [19]

Yavrouian

[11] 4,208,204

[45] Jun. 17, 1980

[54] 3-HYDROXY-3-METHYLGLUTARIC ACID MONOAMIDE AND DERIVATIVES THEREOF

[75] Inventor: Andre H. Yavrouian, Los Angeles, Calif.

[73] Assignee: Calbiochem-Behring Corp., La Jolla, Calif.

[21] Appl. No.: 840,120

[22] Filed: Oct. 7, 1977

[51] Int. Cl.$^2$ .................. A01N 9/20; C07C 121/34; C07C 121/417

[52] U.S. Cl. ......................... 71/97; 71/106; 71/113; 260/429 R; 260/429.9; 260/465.4; 260/465.6; 260/561 B; 560/180; 562/568

[58] Field of Search ............... 260/534 M, 501.1; 71/113, 106; 562/567; 560/170

[56] References Cited

U.S. PATENT DOCUMENTS

| | | | |
|---|---|---|---|
| 952,006 | 3/1910 | Fourneau | 260/534 M |
| 2,530,065 | 11/1950 | King | 260/534 M X |
| 3,386,827 | 6/1968 | Aebi et al. | 96/91 R |
| 3,712,804 | 1/1973 | Muller et al. | 71/113 |
| 3,843,711 | 10/1974 | Wiegand | 260/534 M X |
| 3,857,879 | 12/1974 | Abramitis | 71/113 X |

FOREIGN PATENT DOCUMENTS

| | | | |
|---|---|---|---|
| 531845 | 10/1956 | Canada | 260/534 M |
| 594214 | 3/1960 | Canada | 71/113 |

*Primary Examiner*—Joseph Paul Brust
*Attorney, Agent, or Firm*—Natalie Jensen

[57] ABSTRACT

Disclosed as novel compounds are 3-hydroxy-3-methylglutaric acid monoamide and the lower alkyl esters and salts thereof, 3-hydroxy-3-methylglutaramide mononitrile and 3-hydroxy-3-methylglutaramide. 3-Hydroxy-3-methylglutaric acid monoamide and derivatives thereof exhibit anti-germination and anti-growth utility against a wide variety of perennial and annual weed grasses. 3-Hydroxy-3-methylglutaramide mononitrile and 3-hydroxy-3-methylglutaramide have utility as intermediates in the preparation of 3-hydroxy-3-methylglutaric acid monoamide.

1 Claim, No Drawings

3-HYDROXY-3-METHYLGLUTARIC ACID MONOAMIDE AND DERIVATIVES THEREOF

DESCRIPTION OF THE INVENTION

The present invention relates to novel chemical compounds. More particularly, the present invention relates to compounds of the formula

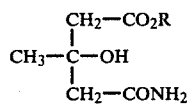
(I)

wherein R is hydrogen, lower alkyl, a metal cation, ammonium, or lower alkyl ammonium.

In addition, the present invention relates to certain compounds obtained as intermediates in the preparation of compounds of formula (I). These novel intermediates are represented by the formulas:

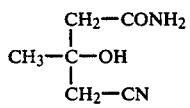   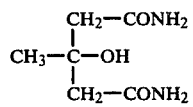

(II)                    (III)

The subject compounds of formula (I) are useful in preventing or controlling undesirable plant growth. More specifically, compounds of formula (I) exhibit anti-germination and anti-growth utility against a wide variety of undesirable weed grasses. For example, compounds of formula (I) inhibit the germination and growth of perennial and annual species of weed grass such as Bearded Wheat, Hares Tail, Sea Oats, Quaking Grass, Animated Oats, Cloud Grass, Feather Grass and the like.

Accordingly, a further aspect of the present invention relates to compositions for agricultural use, which compositions comprise the subject compounds of formula (I) in combination with a suitable carrier. A still further aspect of the present invention relates to methods of inhibiting the germination and growth of weed grasses by applying to soil subject to such growth an effective amount of a compound of formula (I) or a composition containing same.

In agricultural applications the subject compounds of formula (I) may be applied to the soil alone or in admixture with a powdered solid carrier. Typical powdered carriers are the various mineral silicates, e.g., mica, talc, pyrophyllite and clays. As a soil treatment the subject compounds can be applied as a dust in admixture with sand, soil or a powdered solid carrier such as a mineral silicate with or without a surface-active agent, or the subject compounds can be applied as an aqueous spray optionally containing a surface-active dispersing agent and a powdered solid carrier. Compositions containing the compounds of formula (I) exhibit anti-germination and anti-growth activity over a wide range of concentration. In general, compositions containing 1 to 95% by weight of the subject compounds are advantageously employed.

The present invention in a still further aspect is directed to a method for the preparation of compounds of formulas (I), (II), and (III) according to the following reaction sequence:

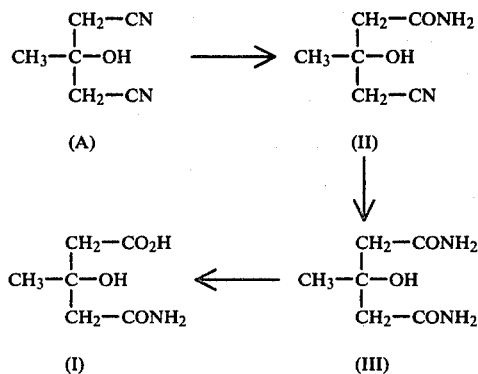

In the above sequence, 3-hydroxy-3-methylglutaronitrile (A) is hydrolyzed in aqueous solution in the presence of acid or base to obtain either the subject compound of formula (I) directly or one or both intermediate compounds of formulas (II) and (III) which can be further hydrolyzed to (I). Base hydrolysis affords significantly better yields and is therefore preferred.

Basic hydrolysis of 3-hydroxy-3-methylglutaronitrile is performed according to the instant invention by treatment of the dinitrile with a base in the presence of a peroxide. Suitable bases include, for example, alkali metal or alkaline earth metal oxides or hydroxides or basic anion exchange resins. Suitable peroxides include, for example, inorganic peroxides such as hydrogen peroxide, sodium peroxide and barium peroxide and organic peroxides such as, for example, benzoyl peroxide.

Direct hydrolysis of 3-hydroxy-3-methylglutaronitrile to (I) with base is conducted at a pH of about 12 to 14 and a temperature from about 20° to 100° C. for about 10 minutes to 3 hours. The reaction preferably employs from about 1 to about 5 moles of base (preferably sodium hydroxide) and from about 1 to about 5 moles of peroxide (preferably hydrogen peroxide) per mole of 3-hydroxy-3-methylglutaronitrile. The resultant product is neutralized to obtain the free acid (I, R=H) which may be purified by conventional means.

Basic hydrolysis of 3-hydroxy-3-methylglutaronitrile to afford (II) and/or (III) is conducted at a pH of about 12 to 14 and a temperature from about 0° to 60° C. for about 10 minutes to 24 hours. The reaction preferably employs from about 1 to 5 moles of base (preferably a basic anion exchange resin such as Dowex 2 in the hydroxide form) and from about 1 to about 5 moles of peroxide (preferably hydrogen peroxide) per mole of 3-hydroxy-3-methylglutaronitrile. The reaction is monitored by high pressure liquid chromatography and is continued until concentrations of (II) and (III) are relatively high and little or no dinitrile remains. The products, i.e., 3-hydroxy-3-methylglutaramide mononitrile (II) and 3-hydroxy-3-methylglutaramide (III) are conventionally separated by ion exchange chromatography and purified by conventional methods.

The intermediates (II) and (III) may be further converted to (I) by basic hydrolysis, preferably utilizing the conditions previously described for converting (A) to (I). Moreover, (II) may be converted to (III) by basic hydrolysis utilizing conditions previously described for converting (A) to (II) and/or (III).

Acid hydrolysis of 3-hydroxy-3-methylglutaronitrile is performed according to the instant invention by treatment of the dinitrile with a strong acid in the presence of a peroxide. Suitable acids include, for example, mineral acids such as hydrochloric acid, hydrobromic acid, sulfuric acid, phosphoric acid, nitric acid, and the like; sulfonic acids such as methanesulfonic acid and p-toluenesulfonic acid; and suitable acid cation exchange resins. Suitable peroxides include those previously enumerated as being useful in basic hydrolysis.

Direct hydrolysis of 3-hydroxy-3-methylglutaronitrile to (I) with acid is conducted at a pH of about −1 to 1 and a temperature from about 20° to 100° C. for about 15 minutes to 24 hours. The reaction preferably employs from about 1 to about 5 moles of acid (preferably hydrochloric acid) and from about 1 to about 3 moles of peroxide (preferably hydrogen peroxide) per mole of 3-hydroxy-3-methylglutaronitrile.

Acid hydrolysis of 3-hydroxy-3-methylglutaronitrile to afford (II) and/or (III) is conducted at a pH of about 0 to 3 and a temperature from about 0° to 60° C. for about 10 minutes to 6 hours. The reaction preferably employs from about 1 to 5 moles of acid (preferably hydrochloric acid) or a cation exchange resin such as Dowex 50 in the hydrogen ion form (a product of the Dow Chemical Company) and from about 1 to about 3 moles of peroxide (preferably hydrogen peroxide) per mole of 3-hydroxy-3-methylglutaronitrile. The reaction is monitored by high pressure liquid chromatography and is continued until concentrations of (II) and (III) are relatively high and little or no dinitrile remains. The products, i.e., 3-hydroxy-3-methylglutaramide mononitrile (II) and 3-hydroxy-3-methylglutaramide (III) are conveniently separated by ion exchange chromatography and purified by conventional means.

The intermediates (II) and (III) may be further converted to (I) by acid hydrolysis, preferably utilizing the conditions previously described for converting (A) to (I). Moreover, (II) may be converted to (III) by acid hydrolysis described for converting (A) to (II) and/or (III).

3-Hydroxy-3-methylglutaronitrile used as a starting material in the above reaction sequence can be prepared according to known procedures found in the literature, such as those cited in *J. Org. Chem.*, 27, pp. 2241–2243 (1962) and *J. Am. Chem. Soc.*, 63, pp. 976–977 (1941).

The present invention in yet a still further aspect is directed to a second method for the preparation of compounds of formula (I) according to the following sequence:

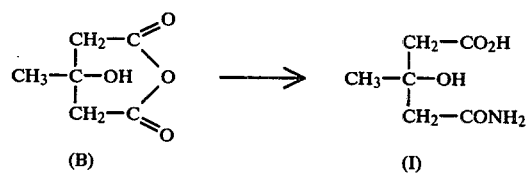

In the above sequence 3-hydroxy-3-methylglutaric acid anhydride (B) is treated with ammonium hydroxide or liquid ammonia, optionally in the presence of an additional solvent at a temperature of 0° to 80° C. for about from 1 minute to 1 hour. Suitable solvents include, for example, methanol, ethanol and dimethyl formamide. The resulting product is neutralized to obtain the free acid which may be purified by conventional means.

3-Hydroxy-3-methylglutaric acid anhydride used in the above sequence is commercially available or can be prepared according to the procedure of H. Hilz, et al., *Biochem. Zeit.*, 329, pp. 476–489 (1958).

The subject compounds embraced by formula (I) include the free acid as well as salts and lower alkyl esters thereof. Accordingly, the present invention in a further aspect relates to conversions between such forms, which conversions are carried out by conventional methods, such as neutralization, saponification, esterification, ester hydrolysis and the like. For example, the lower alkyl esters of 3-hydroxy-3-methylglutaric acid monoamide (I) may be prepared by treatment of the free acid with an ethereal diazoalkane such as diazomethane or with the desired lower alkyl halide in the presence of lithium carbonate at room temperature or with the desired lower alkanol in the presence of a trace amount of acid. The salts of 3-hydroxy-3-methylglutaric acid monoamide (I) may be prepared by treating the free acid with a suitable base. Representative salts derived from such bases include, but are not limited to, the lithium, sodium, potassium, calcium, magnesium, zinc, manganese, barium, ammonium and lower alkyl ammonium salts. The reaction is typically conducted in aqueous solution alone or in combination with a water miscible organic solvent at room temperature.

Alternatively, salts of 3-hydroxy-3-methylglutaric acid monoamide may be prepared by saponification of the lower alkyl esters.

The term "lower alkyl" as used herein refers to a saturated, branched, or unbranched acyclic hydrocarbon group containing 1 to 4 carbon atoms, such as methyl, ethyl, n-propyl, isopropyl, n-butyl, and the like. The term "metal cation" as used herein refers to lithium, sodium, potassium, barium, calcium, magnesium, zinc and manganese cations. The term "lower alkyl ammonium" refers to

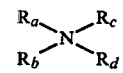

wherein $R_a$, $R_b$, $R_c$ and $R_d$ are independently hydrogen or lower alkyl as defined above with the proviso that at least one of $R_a$, $R_b$, $R_c$ and $R_d$ is lower alkyl.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE 1

A solution of 12.4 g (0.10 moles) of 3-hydroxy-3-methylglutaronitrile in 107 ml of 1.3 M sodium hydroxide is stirred at room temperature while 17.4 ml (0.20 moles) of 30% hydrogen peroxide is slowly added. After the addition of peroxide, the mixture is heated to boiling and boiling is maintained for 2 hours. Thereafter the mixture is cooled, diluted to 1 liter with water and passed through a 200 ml column of Dowex 2 resin in the formate form. The column is then washed with 1 liter of water. Thereafter the product is eluted with 1 liter of 0.1 N formic acid and the eluate evaporated to dryness to afford 3-hydroxy-3-methylglutaric acid monoamide.

The above obtained acid is dissolved in a mixture of 20 ml of 15 N ammonium hydroxide and 100 ml of methanol. The mixture is then evaporated to dryness under vacuum and the resulting ammonium salt dissolved in 25 ml of ethyl acetate containing sufficient isopropyl alcohol to effect solution. The solution is cooled to −20° C. and the ammonium salt which separates is collected by filtration. The salt is then dissolved in 50 ml of methanol and 2 g. of activated carbon is added. The mixture is filtered and the filtrate diluted with 130 ml of ethyl acetate. Upon cooling to 0° C., 3 g. of 3-hydroxy-3-methylglutaric acid monoamide, ammonium salt is obtained as light brown crystals. [m.p. 135°–138° C.; ir (KBr): 3500-3100, 1660, 1610, 1390 cm$^{-1}$; pmr 60 MHz (D$_2$O): 1.7 (3H,s); 2.9 (2H,s); 2.8 (2H,s); 5.2 (7H,s) ppm; Anal. Found: C, 40.49%; H, 7.90%; N, 15.73%; C$_6$H$_{14}$N$_2$O$_4$ requires C, 40.45%; H, 7.87%; N, 15.73%]

EXAMPLE 2

3-Hydroxy-3-methylglutaronitrile (20 g; 0.16 moles), 100 ml of water, 100 ml of moist Dowex 2 (OH$^-$) resin and 20 ml (0.23 moles) of 30% hydrogen peroxide are heated at reflux for 1 hour. Thereafter an additional 20 ml of hydrogen peroxide is added and refluxing is continued. After refluxing for one hour, high pressure liquid chromatography shows almost no 3-hydroxy-3-methylglutaronitrile present. The mixture is then cooled, filtered and concentrated to a volume of 25 ml. The concentrate is applied to a 1.6×20 inch column of Dowex 2 (OH$^-$) resin and elution is carried out with water. The column eluate between 0.5 and 0.7 liters is collected and used in a subsequent example (i.e., Example 3).

The column eluate between 1.0 and 1.4 liters is concentrated under vacuum and the resulting residue dissolved in 20 ml of ethyl acetate. The solution is filtered and then cooled to 0° C. After 24 hours, 2 g. of 3-hydroxy-3-methylglutaramide mononitrile (II) is obtained as a crystalline while solid [m.p. 72°–73° C.; ir (KBr): 3450-3180, 2250, 1660, 1380 cm$^{-1}$; pmr 60 MHz (D$_2$O+DSS): 1.4 (3H,s); 2.5 (2H,s); 2.8 (2H,s) ppm; Anal. Found: C, 50.76%, H, 7.17%; N, 19.64%; C$_6$H$_{10}$N$_2$O$_2$ requires C, 50.69%; H, 7.09%; N, 19.71% ]. DSS=sodium 3-trimethylsilylpropane sulfonate

EXAMPLE 3

The column eluate obtained in the previous example (i.e., eluate collected between 0.5 and 0.7 liters) is concentrated under vacuum and the resulting residue dissolved in 10 ml of hot methanol. The solution is then cooled, filtered and the resulting filtrate diluted with 10 ml of acetone. The small amount of precipitate which forms is removed by filtration and the resulting filtrate is then evaporated under vacuum to dryness. The residue is dissolved in 2 ml of methanol and the solution is then diluted with 5 ml of acetone. After cooling at −20° C., 0.5 g. of 3-hydroxy-3-methylglutaramide (III) is obtained as a crystalline white solid [m.p. 134°–135° C.; ir (KBr): 3450-3100, 1650 cm$^{-1}$; pmr 60 MHz (D$_2$O): 2.0 (2H,s); 3.0 (4H,s); 5.1 (5H,s) ppm; Anal. Found: C, 44.71%; H, 7.58%; N, 16.66%; C$_6$H$_{12}$N$_2$O$_3$ requires C, 44.99%, H, 7.55%, N, 17.49% ].

EXAMPLE 4

Repeating the procedure of Example 1, but replacing 3-hydroxy-3-methylglutaronitrile with 3-hydroxy-3-methylglutaramide mononitrile (II) or 3-hydroxy-3-methylglutaramide (III) is productive of 3-hydroxy-3-methylglutaric acid monoamide (I).

EXAMPLE 5

Repeating the procedure in paragraph 1 of Example 2, but replacing 3-hydroxy-3-methylglutaronitrile with 3-hydroxy-3-methylglutaramide mononitrile, and thereafter repeating the procedure of Example 3 is productive of 3-hydroxy-3-methylglutaramide (III).

EXAMPLE 6

A mixture of 20 g. (0.16 moles) of 3-hydroxy-methylglutaronitrile, 200 ml of water, 32 ml (0.33 moles) of 30% hydrogen peroxide and 70 ml of 12 N hydrochloric acid is stirred at 25° C. for approximately 3 hours and then heated at reflux for 30 minutes. Thereafter the mixture is cooled, diluted to 1 liter with water and the pH adjusted to 7 with 14 N ammonium hydroxide. The mixture is passed through a 250 ml column of Dowex 2 resin in the formate form and the column is then washed with 1 liter of water. Thereafter the product is eluted with 1 liter of 0.1 N formic acid and the eluate evaporated to dryness under vacuum to afford 3-hydroxy-3-methylglutaric acid monoamide.

The above obtained acid may be further characterized by conversion to the ammonium salt as described in Example 1.

EXAMPLE 7

A mixture of 3-Hydroxy-3-methylglutaronitrile (20 g., 0.16 moles), 200 ml of water, 200 ml of moist Dowex 50 (H$^+$) and 32 ml (0.33) moles of 30% hydrogen peroxide is stirred at 25° C. for approximately 3 hours and then heated to 80 C. After heating at 80° C. for 10 minutes, high pressure liquid chromatography shows almost no 3-hydroxy-3-methylglutaronitrile present. The ion exchange resin is then removed by filtration and the filtrate evaporated to dryness. The resulting residue is then dissolved in 25 ml of water and applied to a 1.6×20 inch column of Dowex 2 (OH$^-$) resin. Elution is carried out with water. The column eluate between 1 and 1.5 liters is collected and concentrated under vacuum. The resulting residue is dissolved in ethyl acetate and the solution cooled to 0° C. After 24 hours, 3-hydroxy-3-methylglutaramide mononitrile is obtained as a crystalline white solid.

EXAMPLE 8

A mixture of 3-hydroxy-3-methylglutaronitrile (20 g., 0.16 moles) 200 ml of water, 50 ml of 12 N hydrochloric acid and 32 ml (0.33 moles) of 30% hydrogen peroxide is stirred at 25° C. for approximately 3 hours and then heated to 80° C. After heating at 80° C. for 30 minutes, high pressure liquid chromatography shows almost no 3-hydroxy-3-methylglutaronitrile present. Thereafter, the solution is evaporated to dryness and the residue, dissolved in 25 ml of water, is applied to a 1.6×20 inch column of Dowex 2 (OH$^-$) resin. Elution is carried out with water. The column eluate between 0.5 and 0.7 liters is collected and concentrated under vacuum. The resulting residue is dissolved in 10 ml of hot methanol. The precipitate that forms on cooling is removed by filtration and the resulting filtrate is then diluted with 10 ml of acetone, filtered and evaporated to dryness. The residue is then dissolved in 2 ml of methanol, subsequently diluted with 5 ml of acetone. After cooling at −20° C., 0.3 g of 3-hydroxy-3-methylglutaramide is obtained as a white solid.

EXAMPLE 9

Repeating the procedure of Example 6, but replacing 3-hydroxy-3-methylglutaronitrile with 3-hydroxy-3-methylglutaramide mononitrile (II) or 3-hydroxy-3-methylglutaramide (III), is productive of 3-hydroxy-3-methylglutaric acid monoamide (I).

EXAMPLE 10

Repeating the procedure of Example 8, but replacing 3-hydroxy-3-methylglutaronitrile with 3hydroxy-3-methylglutaramide mononitrile (II), is productive of 3-hydroxy-3-methylglutaramide (III).

EXAMPLE 11

1.7 g. (0.011 moles) of 3-hydroxy-3-methylglutaric acid anhydride (prepared according to the method of Hilz, et al, *Biochem Zeit*, 329, 476–489 (1958)) in 30 ml of 15 N ammonium hydroxide is allowed to stand at 25° C. for 10 minutes. The solution is then evaporated to dryness under vacuum and the resulting residue dissolved in 10 ml of warm methanol. Ethyl acetate (10 ml) is then slowly added to the methanol solution. Upon cooling, 1.5 g. of 3-hydroxy-3-methylglutaric acid monoamide, ammonium salt is obtained as a white crystalline solid.

EXAMPLE 12

1.61 g. (0.01 moles) of 3-hydroxy-3-methylglutaric acid monoamide is dissolved in 25 ml of water and 10 ml of 1 N sodium hydroxide is added to the solution. The resulting mixture is stirred and then evaporated to dryness to afford 3-hydroxy-3-methylglutaric acid monoamide, sodium salt.

In like manner, other salts of 3-hydroxy-3-methylglutaric acid monoamide are prepared by replacing sodium hydroxide with other suitable bases.

EXAMPLE 13

A solution of 1.78 g. (0.01 moles) of 3-hydroxy-3-methylglutaric acid monoamide, ammonium salt in 50 ml of water is passed through a 100 ml column of Dowex 50 (H+) resin. The resulting eluate is then evaporated to dryness to afford 3-hydroxy-3-methylglutaric acid monoamide.

In like manner, all salts of 3-hydroxy-3-methylglutaric acid monoamide can be converted to the free acid by the same, or similar, methodology.

EXAMPLE 14

1.61 g. (0.01 moles) of 3-hydroxy-3-methylglutaric acid monoamide is dissolved in 100 ml of absolute methanol containing 5 g. of hydrogen chloride. After 24 hours at room temperature the reaction mixture evaporated to dryness under vacuum. The residue is then dissolved in 50 ml of water and the solution is passed through a 50 ml column of Dowex 2 in the formate form. The column is eluted with 200 ml of water and the eluate is then evaporated to afford 3-hydroxy-3-methylglutaric acid monoamide, methyl ester.

In like manner, other lower alkyl esters of 3-hydroxy-3-methylglutaric acid monoamide are prepared by replacing methanol with other suitable lower alkanols.

EXAMPLE 15

1.56 g. (0.01 moles) of 3-hydroxy-3-methylglutaric acid monoamide methyl ester is dissolved in 10 ml of 1 N sodium hydroxide. After 24 hours at room temperature the solution is diluted to 50 ml with water and passed through a 50 ml column of Dowex 50 ($H^{30}$) resin. The column is washed with 100 ml of water and the washings collected and evaporated to afford 3-hydroxy-3-methylglutaric acid monoamide.

In like manner, 3-hydroxy-3-methylglutaric acid monoamide is also prepared by the hydrolysis of other lower alkyl esters of the free acid.

EXAMPLE 16

1.79 g. (0.01 moles) of 3-hydroxy-3-methylglutaric acid monoamide, ammonium salt is dissolved in 50 ml of water and the solution is passed through a 100 ml column of Dowex 50 ($H^{30}$) resin. The eluate is evaporated to dryness and the resulting residue dissolved in 100 ml of methanol containing 5 g. of hydrogen chloride. After 24 hours at room temperature the reaction mixture is evaporated to dryness under vacuum. The resulting residue is dissolved in 50 ml of water and the solution passed through a 50 ml column of Dowex 2 in the formate form. The column is eluted with 200 ml of water which is collected and evaporated under vacuum to afford 3-hydroxy-3-methylglutaric acid monoamide, methyl ester.

In like manner, other lower alkyl esters of 3-hydroxy-3-methylglutaric acid monoamide are prepared from the various salts of 3-hydroxy-3-methylglutaric acid monoamide and suitable lower alkanols.

EXAMPLE 17

1.56 g. (0.01 moles) of 3-hydroxy-3-methylglutaric acid monoamide methyl ester is dissolved in 10 ml of 1 N sodium hydroxide. After 24 hours at room temperature the solution is evaporated to dryness to afford 3-hydroxy-3-methylglutaric acid monoamide, sodium salt.

In like manner, other salts of 3-hydroxy-3-methylglutaric acid monoamide are prepared from the various lower alkyl esters of 3-hydroxy-3-methylglutaric acid monoamide and other suitable bases.

EXAMPLE 18

The anti-germinant and anti-growth utility of the subject compounds (I) of the instant invention is illustrated as follows:

Approximately 130 mg. of mixed seeds of perennial and annual weed grasses were planted in each of three 9 cm. Petri dishes packed with terrarium potting soil. The seed mixture (obtained from the Applewood Seed Co., Golden, Colorado) included the following species of weed grass: Bearded Wheat, Hares Tail, Sea Oats, Quaking Grass, Animated Oats, Cloud Grass, and Feather Grass, as well as other unspecified weed grasses.

After planting, seeds in dish #1 were wetted with 10 ml of water; seeds in dish #2 were wetted with 10 ml. of an aqueous 1% solution of 3-hydroxy-3-methylglutaric acid monoamide, ammonium salt; and seeds in Dish #3 were wetted with 10 ml of an aqueous 3% solution of 3-hydroxy-3-methylglutaric acid monoamide, ammonium salt.

Three days after planting, germination was observed in dish #1 but not in dish #2 or #3. Five days after planting approximately 150 seedlings were observed in dish #1; however only 35 and 6 seedlings were observed in dish #2 and dish #3, respectively. The dishes were covered at this time and the seedlings were then watered periodically to maintain uniform moisture levels. Approximately 3 weeks after planting the growth of seedlings in dishes #2 and #3 continued to be very slow and significantly less than the growth exhibited by seedlings in dish #1.

What is claimed is:

1. A method for inhibiting the germination and growth of undesirable weed grasses comprising applying to soil subject to such grasses an effective amount, for said purpose, of a compound of the formula:

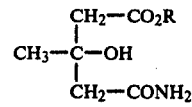

wherein R is hydrogen, lower alkyl, a metal cation selected from the group consisting of lithium, sodium, potassium, barium, calcium, magnesium, zinc and manganese, ammonium or lower alkyl ammonium.

* * * * *